(12) United States Patent
Thompson et al.

(10) Patent No.: US 11,096,820 B2
(45) Date of Patent: Aug. 24, 2021

(54) TISSUE RETENTION DEVICES AND SYSTEMS AND METHODS FOR IMPLANTING AND USING THEM

(71) Applicant: Quiescence Medical, Inc., Dana Point, CA (US)

(72) Inventors: Christopher Paul Thompson, Austin, TX (US); D. Russell Pflueger, Dana Point, CA (US)

( * ) Notice: Subject to any disclaimer, the term of this patent is extended or adjusted under 35 U.S.C. 154(b) by 521 days.

(21) Appl. No.: 15/824,837

(22) Filed: Nov. 28, 2017

(65) Prior Publication Data
US 2018/0168850 A1 Jun. 21, 2018

Related U.S. Application Data

(60) Provisional application No. 62/427,093, filed on Nov. 28, 2016, provisional application No. 62/507,601, filed on May 17, 2017.

(51) Int. Cl.
*A61F 5/56* (2006.01)
*A61B 17/24* (2006.01)

(52) U.S. Cl.
CPC .............. *A61F 5/566* (2013.01); *A61F 5/56* (2013.01); *A61B 2017/248* (2013.01)

(58) Field of Classification Search
CPC ....... A61B 2017/248; A61F 5/56; A61F 5/566
USPC ......................................................... 128/848
See application file for complete search history.

(56) References Cited

U.S. PATENT DOCUMENTS 9,925,086 B2 * 3/2018 Sanders .................. A61F 5/566
2011/0166598 A1 7/2011 Gonazles et al.

FOREIGN PATENT DOCUMENTS

FR 2942954 A1 3/2009

OTHER PUBLICATIONS

European Patent Office, Supplementary European Search Report for corresponding European Application No. 17873012.3-1122, dated Apr. 23, 2020, 7 pages.

* cited by examiner

*Primary Examiner* — Keri J Nelson
(74) *Attorney, Agent, or Firm* — William A. English; Vista IP Law Group LLP (57) ABSTRACT

Systems and methods are provided for treating snoring or sleep apnea of a patient that include an implantable device and a retainer. The device includes an elongate filament sized for introduction into or through a patient's tongue and including a distal end and a proximal end, a connection member on the proximal end, and one or more securing elements on or adjacent the distal end. The retainer includes a body configured to be removably engaged with one or more teeth within a patient's mouth, and a connector port for removably engaging the connection member to support the patient's tongue relative to the retainer.

19 Claims, 8 Drawing Sheets

TISSUE RETENTION DEVICES AND SYSTEMS AND METHODS FOR IMPLANTING AND USING THEM

RELATED APPLICATION DATA

The present application claims benefit of provisional application Ser. No. 62/427,093, filed. Nov. 28, 2016, and 62/507,601, filed. May 17, 2017, the entire disclosures of which are expressly incorporated by reference herein.

FIELD OF THE INVENTION

The present invention relates to devices, systems, and methods for treating snoring and/or sleep apnea, and, more particularly, to implantable devices for implantation at least partially within a patient's tongue that may be detachably coupled to a retainer that may be coupled adjacent patient's teeth, and to systems and methods for implanting and/or using such devices.

BACKGROUND

Sleep apnea is a sleep-related breathing disorder that is thought to affect between one and ten percent (1-10%) of the adult population. Recent epidemiologic data indicate that two percent (2%) of women and four percent (4%) of men between the ages of thirty (30) and sixty (60) years old meet the minimum diagnostic criteria for sleep apnea syndrome, representing more than ten million individuals in the United States. It is a disorder with significant morbidity and mortality, contributing to increased risk of hypertension, cardiac arrhythmias, stroke, and cardiovascular death. Another common sleep-related breathing disorder is snoring, which may be associated with or independent of sleep apnea.

One of the main reasons for sleep disturbance is relaxation of the tongue and pharyngeal walls to varying degrees during the several stages of sleep. When fully awake, these tissues have normal tone as air passes in and out of the lungs during respiration. However, during sleep, the musculature supporting these tissues relaxes. As air is inspired, the tongue and walls of the pharynx collapse, causing snoring or more seriously, causing partial or complete obstruction of the airway.

Obstructive sleep apnea occurs due to a collapse of soft tissue within the upper airway during sleep. The ongoing force of inspiration serves to generate increasingly negative pressure within the pharynx, causing further collapse. The lack of respiration results in inadequate blood oxygenation, and rising carbon dioxide levels. The cardiovascular response produces an increase in blood pressure and pulse. Cardiac arrhythmias often occur. The carbon dioxide increase and oxygen desaturation triggers a transition to a lighter sleep stage, usually without wakefulness. This transition brings a return to tonicity of the muscles of the upper airway, allowing normal breathing to resume. The person then returns to deeper stages of sleep and the process is repeated. The disease is quantified in terms of respiratory disturbances per hour. Mild disease begins at ten per hour, and it is not uncommon to find patients with indices of about one hundred or more.

Not surprisingly, sleep is extremely fragmented and of poor quality in persons suffering from sleep apnea. As a result, such persons typically feel tired upon wakening and may fall asleep at inappropriate times during the day. All aspects of quality of life, from physical and emotional health, to social functioning are impaired by obstructive sleep apnea.

Continuous Positive Airway Pressure ("CPAP") is a popular non-surgical treatment for patients suffering from sleep apnea. CPAP is administered by means of a mechanical unit that delivers pressurized room air to the nasal passage, or airway, through a nose mask that is worn by the patient during sleep. Pressurized air enters from the CPAP unit through the nose when a person is sleeping, and opens the airway from the inside almost as if the air were an internal splint. The correct pressure for the individual is determined in a sleep laboratory. If the nasal airway admits the flow of air, CPAP has in many cases offered immediate relief. Unfortunately however, compliance with, and long-term acceptance of this treatment are generally poor. Studies have shown that between twenty and fifty percent (20-50%) of patients fail to use nasal CPAP as prescribed. Problems associated with CPAP include excessive dryness of the mouth and throat, mucous congestion, sinusitis, and rhinorrhea. Breathing against positive air pressure is also discomforting to many patients.

Other non-surgical treatments for sleep apnea include the use of tongue retaining devices and other oral appliances that hold and/or pull the tongue or jaw in a forward position to open the airway by reducing collapse of the soft palate and/or tongue. These devices also suffer from poor compliance rates, and are usually associated with degenerative changes in the temporomandibular joint.

Surgical procedures have also been proposed and/or practiced for the treatment of moderate to severe sleep apnea. Uvulopalatopharyngoplasty ("UPPP") is a surgical procedure used to treat obstructive sleep apnea. In UPPP, any remaining tonsillar tissue and a portion of the soft palate is removed. The procedure increases the width of the airway at the throat opening. However, UPPP does not address apnea caused by obstructions deeper in the throat and airway, for example, apnea resulting from collapse of tissue near the base of tongue or in the oropharyngeal region of the airway.

LAUP, or Laser-Assisted Uvulopalatoplasty, is a modification of the above-mentioned technique, but has not proven particularly useful for sleep apnea. These surgical techniques are extremely invasive, requiring general anesthesia, and a prolonged, painful recovery.

Radio frequency tissue ablation ("RFTA") has also been suggested for shrinking the soft palate, uvula and reducing tongue volume in the treatment of snoring and obstructive sleep apnea. Somnoplasty utilizes a radiofrequency tool that generates heat to create coagulative lesions at specific locations within the upper airway. The lesions created by the procedure are naturally resorbed in approximately three to eight weeks, reducing excess tissue volume and increasing the airway opening. Like UPPP and LAUP, more than one session is typically required and it does not address sleep apnea resulting from tissues deeper in the throat than the upper airway.

Techniques have also been developed for treating, specifically, the condition of snoring. For example, U.S. Pat. No. 6,250,307 to Conrad et al. discloses a method for treating snoring of a patient that includes embedding a fibrosis-inducing implant into a soft palate of a patient in order to alter a dynamic response of a soft palate to airflow.

Concepts relating to implants in the pharyngeal area have been described in German publication DE 19,920,114 to Fege, published Nov. 9, 2000, which discloses transverse implant bands attached at one end to the cervical vertebra via surgical slits through the tongue, tonsils, and pharyngeal tissue. Other pharyngeal implants have been described in U.S. Publication No. 2003/0149488 to Metzger et al., now U.S. Pat. No. 7,017,582.

Accordingly, devices and methods for treating sleep apnea and/or reducing scoring would be useful.

SUMMARY

The present invention is directed to devices, systems, and methods for treating human subjects, for example, to substantially eliminate or at least reduce the occurrence of sleep apnea, snoring, and/or other sleep-related breathing disorders. More particularly, the present invention is directed to implantable devices for implantation at least partially within a patient's tongue that may be detachably coupled to a retainer that may be coupled adjacent patient's teeth, and to systems and methods for implanting and/or using such devices.

In accordance with one embodiment, a device is provided for treating sleep apnea or snoring that includes a filament comprising a distal end for introduction into a tongue of the patient, and a proximal end including a connection member; and a connector port configured to be located in the oral cavity adjacent the patient's lower middle teeth for receiving the connection member.

In accordance with another embodiment, a system is provided for treating snoring or sleep apnea of a patient, that includes an implantable device comprising an elongate filament sized for introduction into or through a patient's tongue and including a distal end and a proximal end, a connection member on the proximal end, and one or more securing elements on or adjacent the distal end; and a retainer comprising a body configured to be removably engaged with one or more teeth within a patient's mouth, a connector port for removably engaging the connection member to support the patient's tongue relative to the retainer.

In accordance with still another embodiment, a method is provided for treating sleep apnea or snoring that includes introducing a distal end of a filament into a tongue adjacent to the frenulum such that a proximal end of the filament exits the tongue adjacent the frenulum; and attaching a connection member to the proximal end of the filament shaped for coupling to a connector port located adjacent to the lower middle teeth of the patient.

In accordance with yet another embodiment, a method is provided for treating snoring or sleep apnea of a patient that includes introducing a distal end of a filament into a tongue adjacent the frenulum such that a proximal end of the filament exits the tongue adjacent the frenulum and a distal end of the filament exits a posterior region of the tongue; coupling a retention member to the distal end of the filament; partially withdrawing the filament to engage the retention member with the posterior region of the tongue; and providing a connection member on the proximal end of the filament for removably securing the proximal end to a connector port provided adjacent lower teeth of the patient.

In accordance with still another embodiment, a method is provided for treating snoring or sleep apnea of a patient using a filament implanted in the patient's tongue such that a proximal end of the filament exits the tongue adjacent the frenulum, the method comprising placing a retainer with the patient's oral cavity such that a connector port is disposed adjacent front lower teeth of the patient; and coupling a connection member on the proximal end of the filament to the connector port.

These and other aspects of the present invention are apparent in the following detailed description and claims, particularly when considered in conjunction with the accompanying drawings in which like parts bear like reference numerals.

BRIEF DESCRIPTION OF THE DRAWINGS

The present invention is best understood from the following detailed description when read in conjunction with the accompanying drawings. It will be appreciated that the exemplary devices shown in the drawings are not necessarily drawn to scale, with emphasis instead being placed on illustrating the various aspects and features of the illustrated embodiments.

DETAILED DESCRIPTION OF THE EXEMPLARY EMBODIMENTS

The present invention is directed to devices, systems, and methods for treating snoring and/or sleep apnea. More particularly, the present invention is directed to implantable devices for implantation at least partially within a patient's tongue that may be coupled to a connector port in the oral cavity adjacent to the patient's lower middle teeth, and to systems and methods for implanting and/or using such devices.

Figure 1:
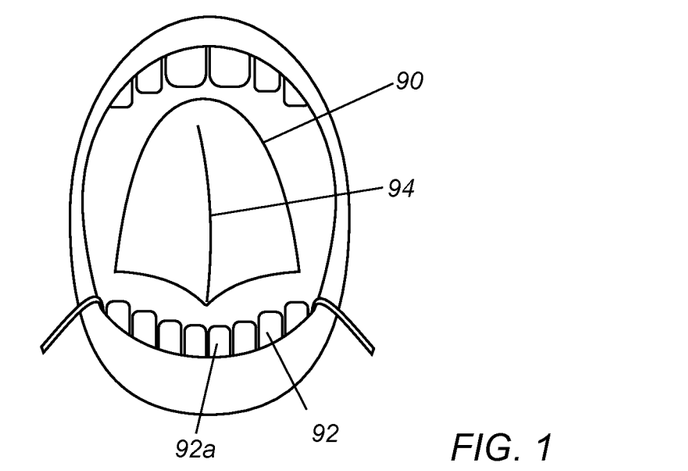
FIG. 1 is a partial cross-sectional view of a mouth showing a tongue and frenulum.
Figure 2:
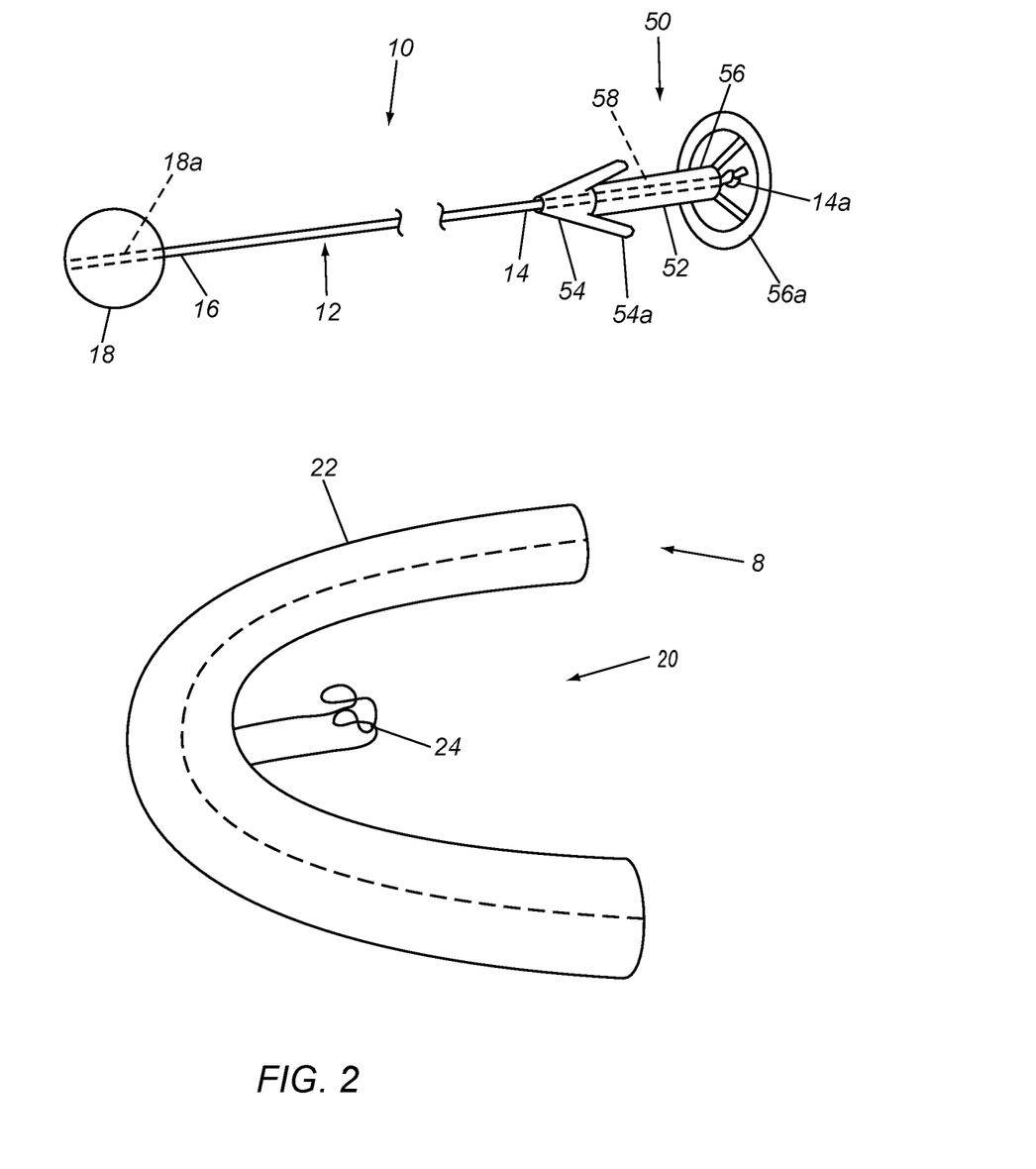
FIG. 2 is a perspective view of a system for supporting a tongue including an implantable device and a retainer.

Turning to the drawings, FIG. 2 shows an exemplary system 8 for treating sleep apnea and/or snoring that includes an implantable device 10 that may be implanted into or through a patient's tongue 90, e.g., via the frenulum 94, and a retainer 20 that may be placed within the patient's oral cavity, e.g., removably engaged with one or more teeth 92, and detachably coupled to the device 10, e.g., during periods of sleep, as shown in FIGS. 1 and 3A-3C and described further elsewhere herein.

Figure 2A:
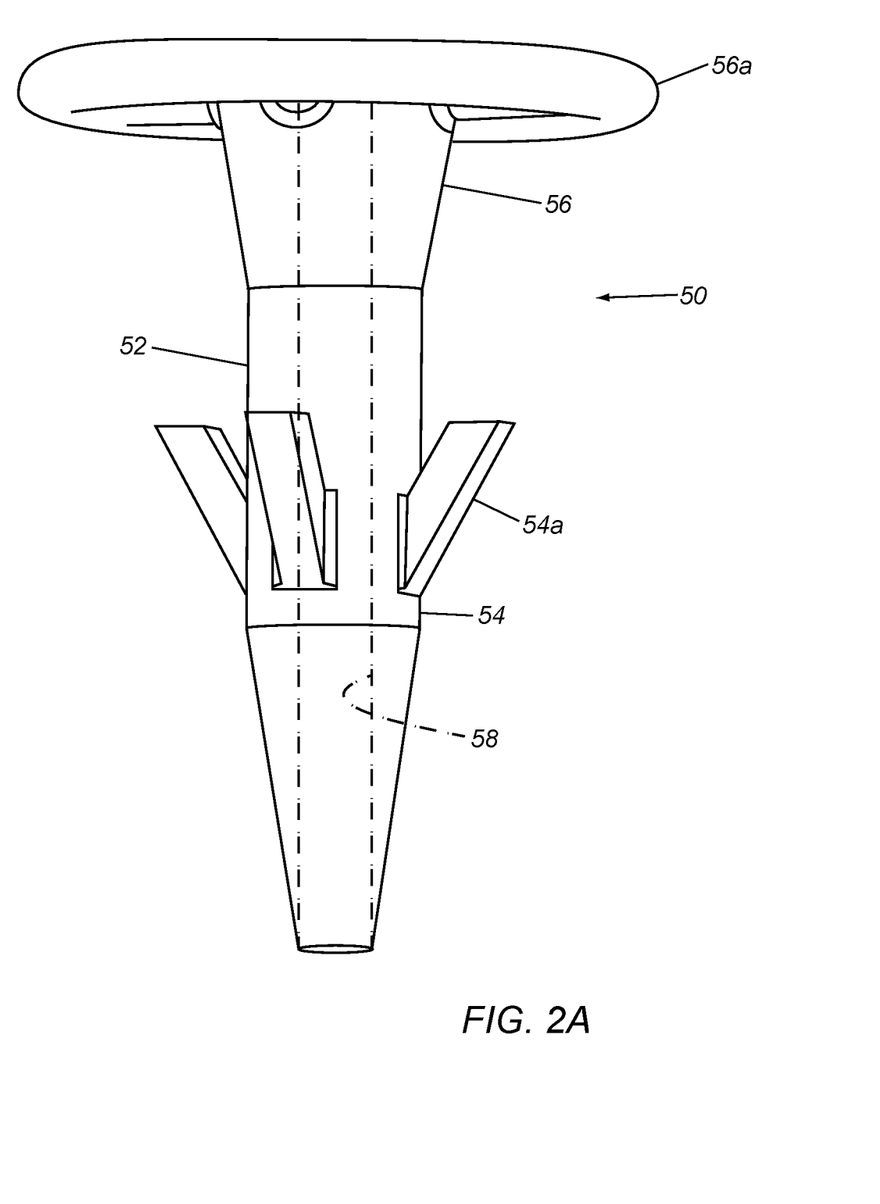
FIGS. 2A and 2B are details of a distal retention member that may be included in the implantable device of FIG. 2.
Figure 2B:
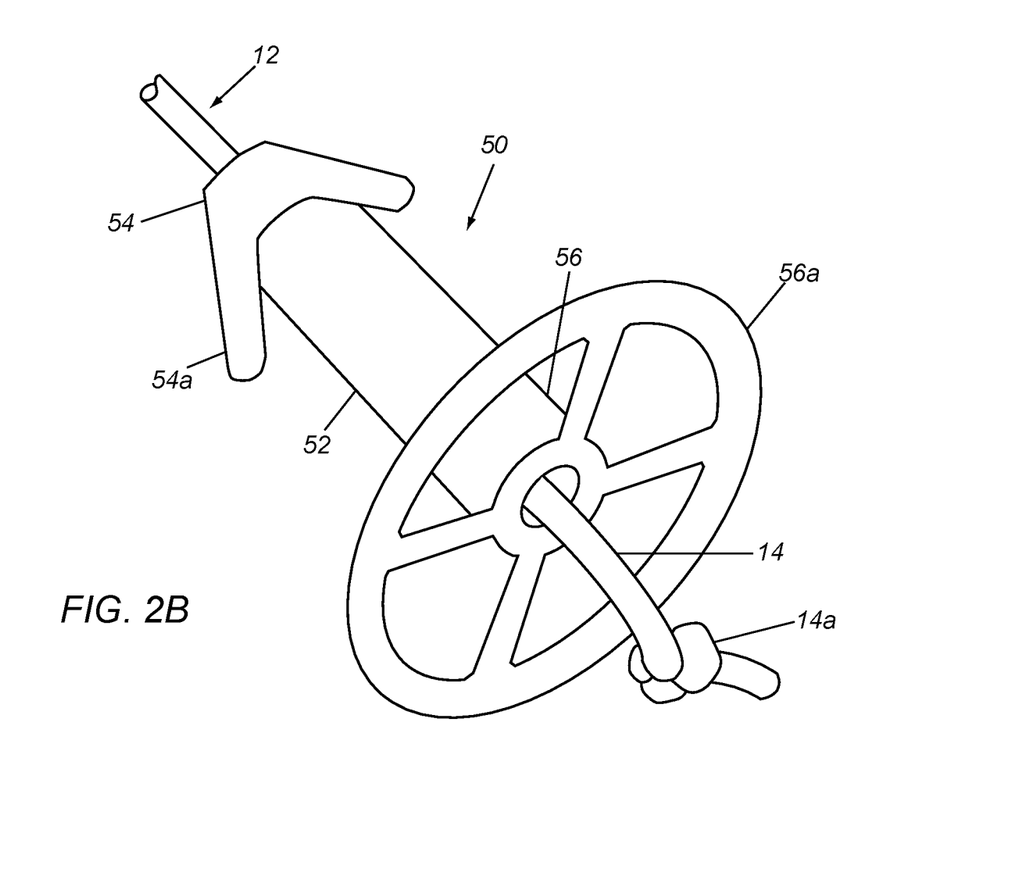
Figure 3A:
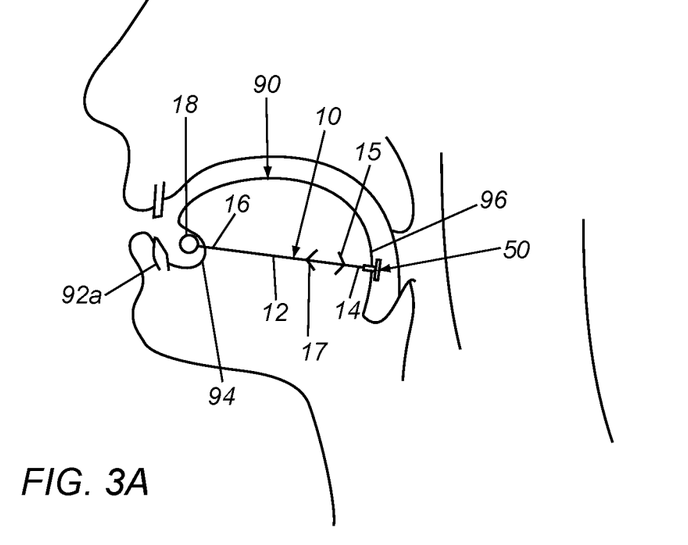
FIGS. 3A and 3B are cross-sectional view of a head showing an exemplary embodiment of an implantable device for supporting a tongue.
Figure 3B:
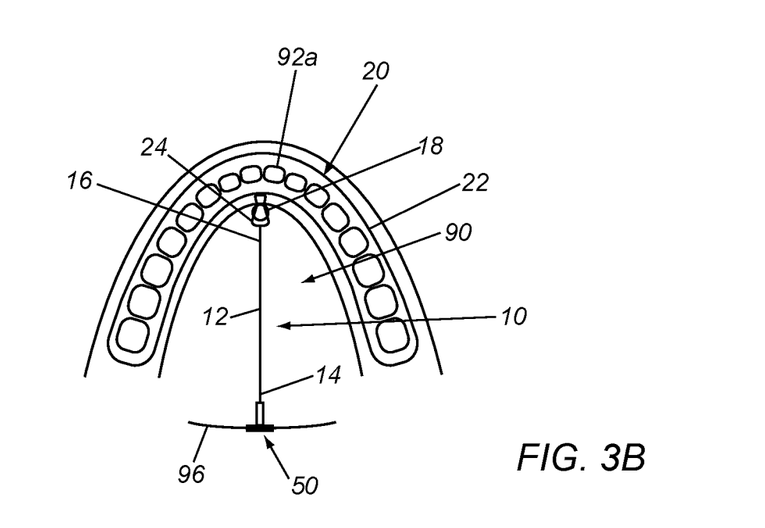
Figure 4:
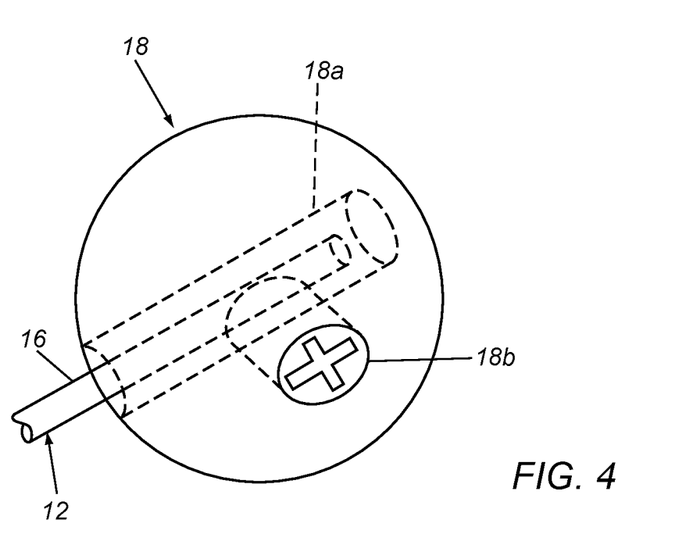
FIG. 4 is a detail showing an exemplary embodiment of a connector member that may be provided on one end of the implantable device of FIG. 2.

With additional reference to FIGS. 2-3, the device 10 generally includes an elongate filament 12 including a distal end 14, which may be secured within and/or relative to the tongue 90, and a proximal end 16 including a connection member 18, e.g., a ball or other generally spherical member, a hemispherical member, a hook, a disc, a loop, and the like, such as the connection member 18 shown in FIG. 4, which may be located near a patient's lower middle teeth 92a after the device 10 is implanted. In an exemplary embodiment, the filament 12 may be an elongate, flexible filament, such as a suture, e.g., formed from plastic, metal, such as Nitinol, or other biocompatible and/or non-bioabsorbable material. The connection member 18 may have a diameter or other cross-section to prevent the connection member 18 from entering the tongue 90 and/or may have an atraumatic shape to prevent discomfort or irritation due to contact with the tongue and/or other tissues within the oral cavity.

Figure 3C:
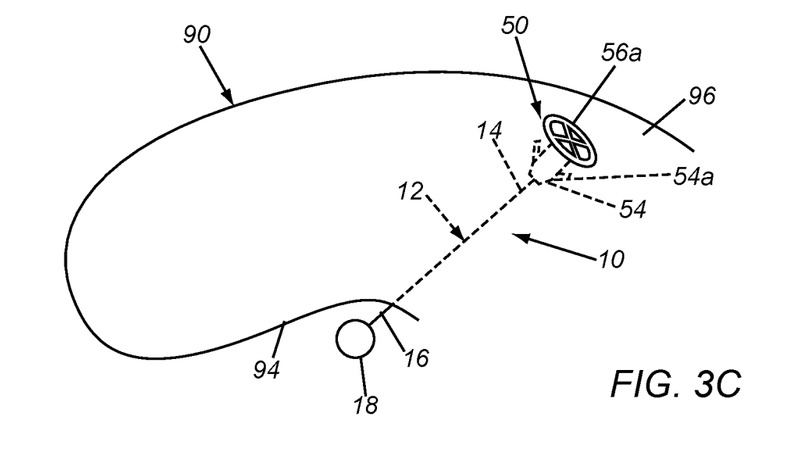
FIG. 3C is a detail showing the retention member of the implantable device of FIGS. 2-2B being secured to a distal region of a tongue.

FIGS. 2A and 2B show an exemplary embodiment of a retention member 50 that may be attached to and/or otherwise carried on the distal end 14 of the filament 12. As shown, the retention member 50 includes an elongate tubular body 52 including a proximal end 54 including a plurality of barbs 54a and a distal end 56 including an enlarged stop or end 56a. For example, the proximal end 54 may be sized to be directed into a patient's tongue, e.g., from a posterior region 96, e.g., as shown in FIG. 3A. Optionally, the proximal end 54 may include a tapered tip, e.g., to facilitate introduction into the patient's tongue. The barbs 54a may be biased to extend transversely, e.g., radially outwardly and distally, yet may be collapsible to accommodate introduction of the proximal end 54 into the tongue and biased to automatically expand to engage surrounding tissue, e.g., to prevent distal movement out of the tongue, as described elsewhere herein. Alternatively, the barbs 54a and/or the entire retention member 50 may be substantially rigid. In a further alternative, the tubular body 52 may include one or more tissue in-growth features, e.g., instead of or in addition to the barbs 54a. The stop 56a on the distal end 56 may be sized to engage the posterior region 96 of the tongue 90, e.g., as shown in FIGS. 3A-3C, to prevent the entire retention member 50 from being pulled into the tongue, also as described further elsewhere herein. As shown, the stop 56a is a ring coupled to the distal end 56 by a plurality of spokes; however, it will be appreciated that other shapes and/or ends may be provided, e.g., a flat head, a spherical or hemispherical member, or other shaped member (not shown) having sufficient contact surface to engage the posterior region 96 of the tongue 90 and prevent the entire retention member 50 from being pulled into the tongue 90, e.g., as shown in FIG. 3C.

The elongate body 52 may include a lumen or passage 58 extending between the proximal and distal ends 54, 56, e.g., to receive at least the distal end 14 of the filament 12 therethrough. For example, the retention member 50 may be provided initially separate from the filament 12, and, after directing the distal end 14 of the filament 12 into and/or through the tongue 90, e.g., from the frenulum 94 through the posterior region 96, the distal end 14 may be directed through the lumen 58 and secured relative to the retention member 50, e.g., using one or more knots 14a, as shown in FIG. 2B and as described further elsewhere herein.

Optionally, the filament 12 may include one or more additional securing elements, e.g., one or more barbs and/or tissue in-growth features, that may enhance securing the filament 12 relative to adjacent tissue. For example, a plurality of one-directional barbs (not shown) may be provided that are spaced apart along a desired length of the filament 12 at least partially between the proximal and distal ends 16, 14, e.g., along a distal portion adjacent the distal end 14. For example, in one embodiment, a plurality of proximally oriented barbs 15 may be integrally formed in the filament 12, e.g., similar to barbed sutures, adjacent the distal end 14 that allow the distal end 16 to be introduced into the tongue 90 from the frenulum 94 but, thereafter, resist the distal end 14 of the filament 12 from being pulled proximally out of the tongue 90. In an alternative embodiment, a plurality of one-directional barbs may be provided on the filament without the retention member 50.

In addition or alternatively, the filament 12 may include one or more features to resist the filament 12 from migrating distally in the tongue 90. For example, as shown in FIG. 2A, the filament 12 may include one or more distally oriented barbs or hooks 17 that may prevent the filament 12 from moving distally once deployed in the tongue 90.

Figure 5:
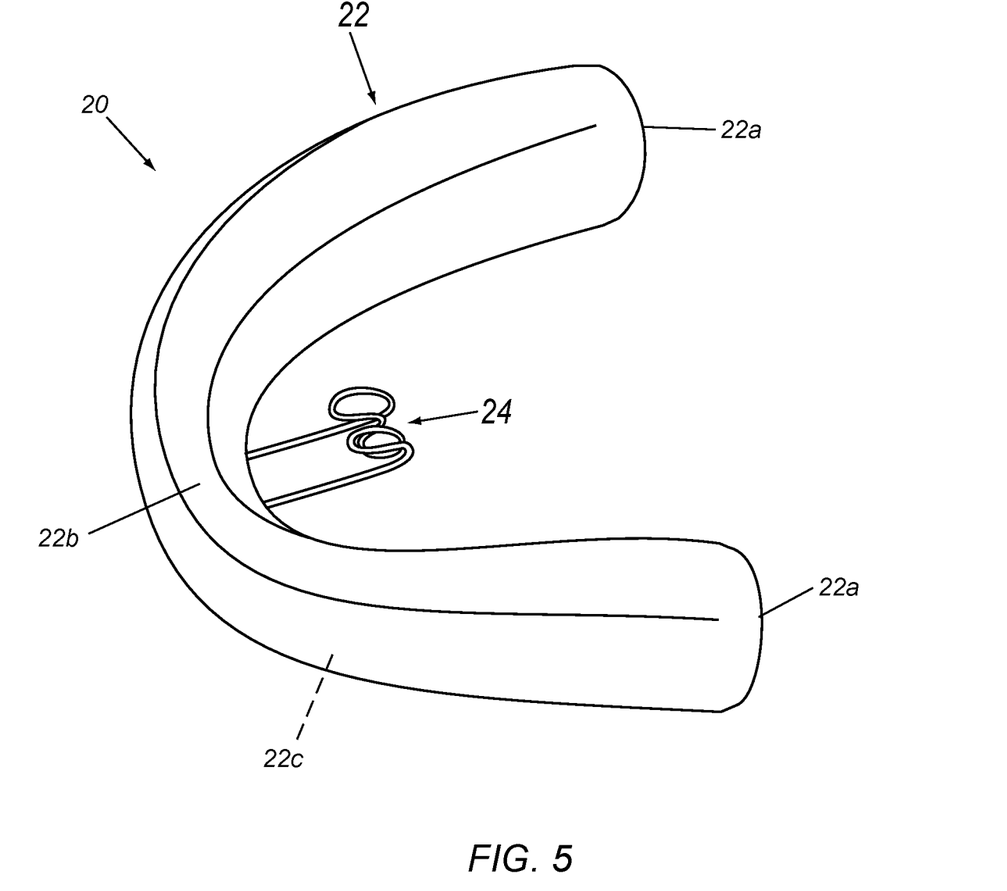
FIG. 5 is a perspective view of an exemplary embodiment of a retainer including an integral connector port.

Returning to FIG. 2, the retainer 20 generally includes a body 22 configured to be removably engaged with one or more teeth 92 within a patient's oral cavity, and a connector port 24 for removably engaging the connection member 18 of the filament 12 to support the patient's tongue relative to the retainer 20. For example, the body 22 may be formed from metal, plastic, and/or composite and biocompatible material that is shaped to at least partially surround the front and backs of the lower teeth 92, e.g., fabricated by standard techniques to fit over and/or around a patient's lower teeth. In exemplary embodiments, the retainer body 22 may have a generally curved or arcuate shape, e.g., including first and second ends 22a and an intermediate region 22b, resembling a wire retainer or an acrylic bite guard, e.g., as shown in FIG. 5. The body 22 may include a recess 22c under the body 22 that extends between the first and second ends 22a, that has a size such that one or more molars of the patient are received in the body 22 adjacent the ends 22a and front teeth are received at the intermediate region 22b, although alternatively, the body 22 may be sized to only extend partially from the front teeth towards the molars.

The connector port 24 may be substantially permanently attached to the body 22, e.g., at an intermediate location corresponding to front lower teeth 92a of the patient, such that the connector port 24 extends towards the patient's tongue when the retainer 20 is placed in the patient's mouth. Thus, the retainer 20 may be temporarily located in the oral cavity adjacent the lower middle teeth 92 with the connector port 24 oriented towards the frenulum 94 and the connection member 18. In an exemplary embodiment, the connector port 24 may be formed from rigid wire formed into a hook or other curved shape to receive the connection member 18 with ends of the wire substantially permanently attached to the body 22, e.g., by one or more of integrally molding the connection member 18 into the body 22, bonding with adhesive, fusing, and the like. Alternatively, the connection member 18 may be integrally molded from the same material as the body 22 and/or may be separately molded, cast, or otherwise formed, and attached to the body 22.

Alternatively, a connector port (not shown) may be substantially permanently fastened directly to the back of the lower teeth 92 or the patient's mandible (also not shown), e.g., using one or more of bonding with adhesive, mechanical connectors, such as a screw, and the like. In another alternative, the connector port may be permanently connected to the connection member 18 of the filament 12.

The connector port 24 is configured to removably receive and/or secure the connection member 18 to support the patient's tongue relative to the retainer 20 and, therefore, relative to the patient's oral cavity. Alternatively, the connector port and connection member may include one or more other connectors that may be removably secured together, e.g., cooperating hooks, loops, magnets and the like (not shown).

Figure 6:
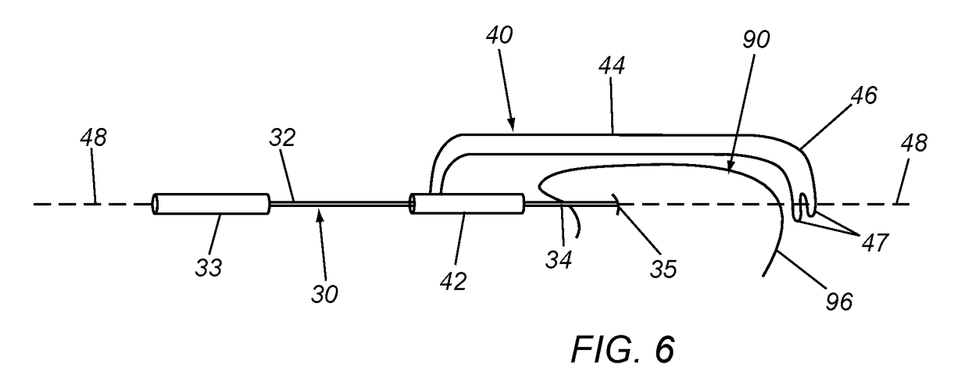
FIG. 6 is a side view of an exemplary embodiment of a cannula and a guide tool including a guide member for introducing an implantable device, such as the implantable device of FIG. 2, into a patient's tongue.
Figure 7:
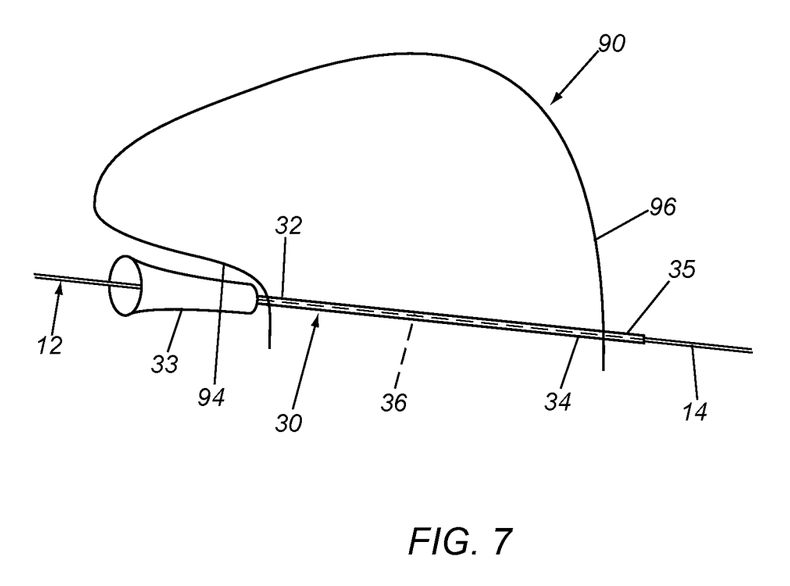
FIG. 7 is a cross-sectional view of a tongue showing a cannula inserted into the tongue, e.g., adjacent the frenulum, to guide a filament into the tongue.

With additional reference to FIGS. 6 and 7, the system 8 may also include one or more tools to facilitate implantation of the device 10. For example, FIG. 6 shows an exemplary embodiment of a trocar and/or cannula 30 and a guide tool 40 that may be included in the system 8. Generally, the cannula 30 includes a proximal end 32 including a handle or hub 33 and a distal end 34 sized for introduction into the patient's tongue 90, e.g., as shown in FIG. 7, including a beveled, tapered, or otherwise sharpened distal tip 35. The cannula 30 also includes a lumen 36 extending between the proximal and distal ends 32, 34 sized for receiving at least the distal end 14 of the filament 12 therein. The guide tool 40 may include a tubular member 42 sized to slidably receive the cannula 30 therethrough, and an elongate guide member 44 extending distally from the tubular member 42, e.g., offset from but extending substantially parallel to a central axis 48 of the tubular member 42. The guide member 44 may terminate in a stop 46, e.g., a bent tip including a pair of tines 47 straddling the central axis 48. In this manner, the cannula 30 may be inserted through the tubular member 42 and parallel to the guide member 44 until the distal tip 35 passes between the tines 47. The guide member 44 may have a length corresponding to the length of the cannula 30 such that the handle 33 of the cannula 30 abuts the tubular member 42 to prevent further distal advancement of the cannula 30 when the distal tip 35 has passed a predetermined distance distal to the stop 46.

During use, a doctor or other health care provider may implant the device 10 within a tongue 90 of a patient, e.g., with the aid of the cannula 30 and/or guide tool 40. Generally, the distal tip 35 of the cannula 30 may be punctured and inserted through the front mid-line of the tongue 90 just above or adjacent to the frenulum 94 in a posterior direction, e.g., near the median raphe, e.g., as shown in FIG. 7. Optionally, before inserting the cannula 30, the guide tool 40 may be positioned over the tongue 90 with the stop 46 located against the posterior region 96 of the tongue 90 and the tubular member 42 proximal to the front of the tongue 90, as shown in FIG. 6.

The cannula 30 may then be inserted through the tubular member 42, into and through the tongue 90 with the tubular member 42 facilitating directing the distal tip 35 of the cannula 30 more easily and precisely towards the back of the tongue 90, e.g., until the distal tip 35 penetrates the posterior region 96 and the handle 33 prevents further advancement, e.g., reducing the risk of puncturing or otherwise damaging adjacent tissue such as the pharynx through the back of the tongue 90. In another alternative, the stop 46 of the guide member 44 may block advancement of the distal tip 35 beyond the guide member 44.

The distal end 14 of the filament 12 (without the retention member 50) may be inserted through the lumen 36 of the cannula 30 until the distal end 14 exits the distal tip 35 at the posterior region 96 of the tongue 90, e.g., as shown in FIG. 7. Alternatively, the filament 12 may be preloaded within the cannula 30 and introduced simultaneously with the cannula 30 and then a length of the distal end 14 may be advanced from the distal tip 35. Once sufficient length of the distal end 14 is exposed, the distal end 14 of the filament 12 may be held, e.g., with a tool or the doctor's fingers (not shown), and the cannula 30 may be withdrawn, leaving the filament 12 passing from the frenulum 94 through the tongue 90 and out the posterior region 96.

The retention member 50 may then be attached to the distal end 14 of the filament 12, e.g., by loading the distal end 14 through the tubular member 52 from the proximal end 54 to the distal end 56 and then tying one or more knots 14a, e.g., as shown in FIG. 2B. Any excess filament may be cut or otherwise separated, and then the filament 12 may be pulled proximally to direct the proximal end 54 and barbs 54a of the retention member 50 into the tongue 90 adjacent the posterior region 96, e.g., until the stop 56a abuts or otherwise engages the tongue 90 and prevents further withdrawal, as shown in FIG. 3C.

If the connection member 18 is provided on the proximal end 16 of the filament 12 before the filament 12 is introduced into the tongue 90, the length of the filament 12 may be set such that the connection member 18 is located under the patient's tongue 90 and/or otherwise adjacent the frenulum 94 when the retention member 50 engages the tongue 90. Alternatively, the filament 12 may be introduced without the connection member 18, and the connection member 18 may be coupled to the proximal end 16 after implantation.

For example, with both the proximal and distal ends 16, 14 free of the connection member 18 and retention member 50, the filament 12 may be introduced through the cannula 30 until both ends exit opposite sides of the tongue 90. The retention member 50 may be attached to the distal end 14, the filament 12 pulled to engage the retention member 50 with the posterior region 96 of the tongue 90, and then the connection member 18 may be attached to the proximal end 16 of the filament 12.

Figure 8:
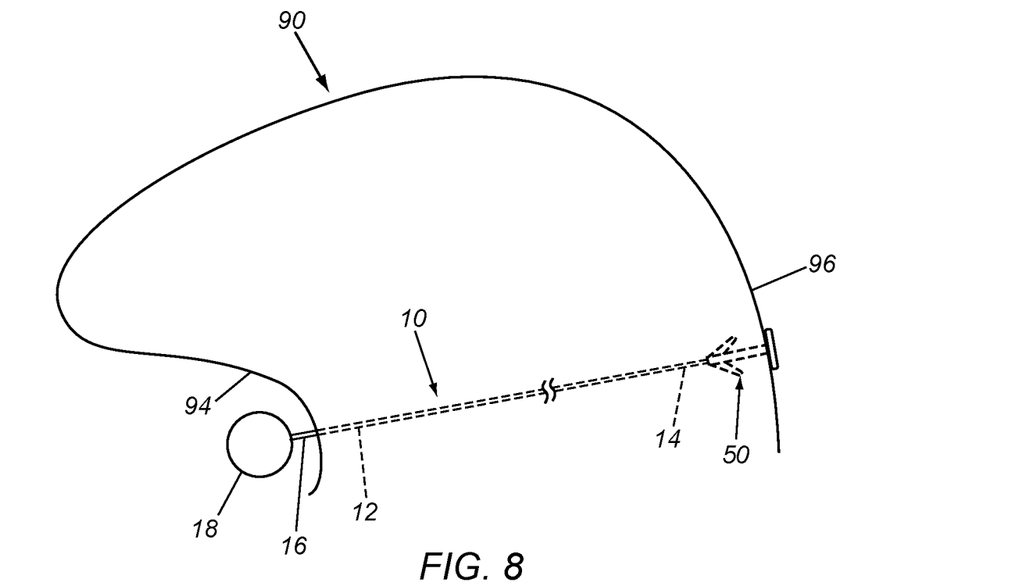
FIG. 8 is a cross-sectional view of a tongue showing an implantable device including a filament implanted within the tongue such that a connector member is disposed adjacent the frenulum.
Figure 9:
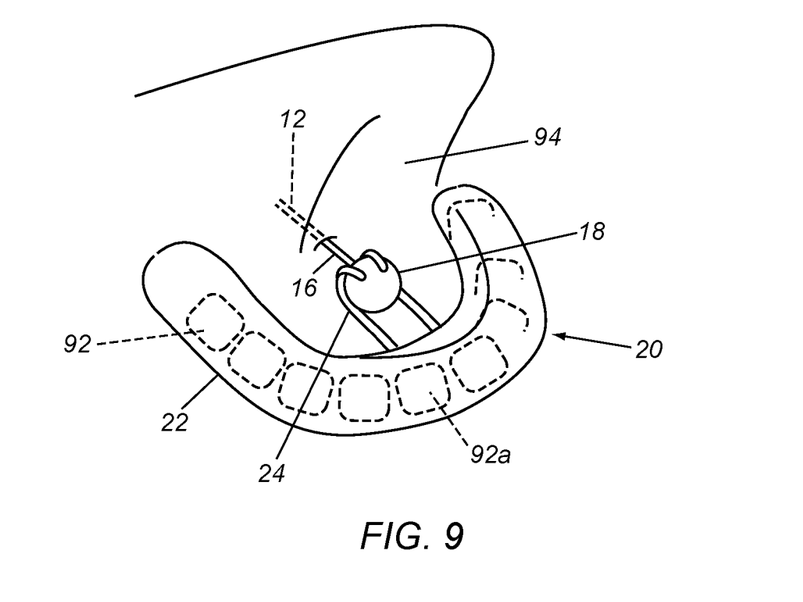
FIG. 9 is a detail showing the connection member of FIG. 8 coupled to a connector port on a retainer placed over the patient's lower teeth.

For example, as shown in FIG. 4, the connection member 18 may be a spherical or otherwise atraumatically shaped member including a passage 18a therethrough into which the proximal end 16 may be introduced. Excess filament material may be cut or otherwise removed, and the connection member 18 attached to the proximal end 16, e.g., using one or more of an adhesive, mechanical engagement, e.g., crimping or knotting, one or more mechanical fasteners, such as the set screw 18b shown in FIG. 4, and the like. FIGS. 8 and 9 show an exemplary embodiment of a filament 12 implanted within a tongue 90 such that the connection member 18 is disposed adjacent the frenulum 94 and lower teeth 92. Alternatively, the proximal end 16 of the filament 12 may include a loop (not shown) to directly connect to the connection port 22, e.g., a post or hook, without the need for the connection member 18.

In an alternative embodiment, the cannula 30 is directed only partially through the tongue 90, e.g., such that a distal tip 35 of the cannula 30 does not penetrate through the back of the tongue 90 but is spaced a desired distance from the back of the tongue 90. The filament 12 may be introduced through a lumen or channel of the cannula 30 until the distal end 14 of the filament 12 is positioned at a desired location within the tongue 90. For example, FIG. 7 shows an exemplary embodiment of a cannula 30 introduced into a tongue 90, e.g., from a location adjacent the frenulum 94, and directed partially towards the back of the tongue 90. Once the filament 12 is positioned within or through the tongue 90 as desired, the cannula 30 (and tool 40) may be removed, thereby exposing the distal end 14 and any barbs thereon within the tongue 90 to anchor the distal end 14 relative to the tongue 90. As shown, the path along which the filament 12 is implanted is substantially straight, although, alternatively, the cannula 30 may have a curved shape, e.g., to reach desired locations in the tongue 90 and/or to provide additional holding strength.

The length of the filament 12 may be selected such that the proximal end 16 exits the tongue 90 at the entrance of the passage created into the tongue 90 adjacent the teeth 92. Alternatively, the filament 12 may be introduced directly into the tongue 90, e.g., by coupling the distal end 14 to a needle or other tool that may be directed into the tongue 90 to pull the filament 12 through the tongue tissue to the desired location.

Optionally, multiple tongue retention devices may be employed to reach desired locations in the tongue or to provide additional holding strength. For example, multiple filaments may be implanted within the tongue that include distal ends that are introduced into different regions of the tongue, i.e., spaced apart from one another to support the respective regions. The proximal ends may be disposed adjacent one another, e.g., exiting the same location of the tongue 90 and coupled to a common connector member (e.g., by inserting the proximal ends through the passage 18a in the connection member 18 shown in FIG. 4 and securing the proximal ends therein).

Once the device 10 (and/or filaments 12) are implanted within or through the patient's tongue, the retainer 20 may be used to resist and/or prevent the tongue 90 from falling back during sleep. For example, as shown in FIG. 9, the retainer 20 may be placed over the teeth 92 and/or otherwise positioned in the patient's oral cavity, and then the connection member 18 may be engaged with the connector port 22. For example, the connector port 22 may include a hook or recess within which the ball connection member 18 may be received after pulling the filament 12 slightly forward, thereby keeping the tongue 90 from falling backwards into the patient's airway and/or pulling the tongue 90 slightly forward.

The connection member 18 may be secured within the connection port 22 simply by distal bias of the tongue 90 and/or may be secured by one or more connectors (not shown) that may be engaged to prevent removal until disconnected. For example, the connection member 18 may be disposed under the tongue when not engaged, e.g., where the proximal end 16 of the filament 12 exits the tongue 90, e.g., near the frenulum 94.

The resulting tongue retention device 10 should provide enough strength to retain the tongue 90 from blocking the airway by moving in a posterior direction during sleep. The securing elements 15, 17 may be designed to prevent the device 10, e.g., the distal end 14 and/or intermediate region of the filament 12 from slipping anteriorly or posteriorly within the tongue 90.

Optionally, the device 10 may be adjustable after implantable, e.g., to adjust the length of the filament 12 and/or the location of the connection member 18. For example, if, after implantation, the patient finds that the tongue 90 is not sufficiently supported, the connection member 18 may be removed, the filament shortened, e.g., by cutting off a desired length of the proximal end 16, and the connection member 18 (or a new one) attached to the remaining proximal end 16. The connection member 18 may allow for easy removable connection to the connector port 22, e.g., such that patient can easily disengage the connection member 18 from the connector port 22 and then remove the retainer 20, e.g., after waking or at an intermediate time, as desired.

In another option, the coupling between the connection member 18 and connector port 22 may allow for adjustments in length, e.g., using a bridge member, e.g., a band, loop, chain, and the like, formed from rubber, fabric, plastic, metal, and the like. The bridge member may be elastic to provide comfort or a persistent forward force on the filament 12.

In yet another alternative, an elastic bridge member (not shown) may be provided on the proximal end 16 between the filament 12 and the connection member 18 and/or between the connection member 18 and the connector port 22. For example, in one alternative, the filament 12 may also be relatively shorter such that the bridge member partially enters into the tongue 90. During use, the connection member 18 may be pulled to elastically stretch the bridge member to allow the connection member 18 to be engaged with the connector port 22. Upon release, the bridge member may resiliently recoil to apply a desired tensile force to the filament 12 and secure the connection member 18. Alternatively, an elastic filament 12 or elastic bridge member may be permanently connected between the connection member 18 and the connector port 22.

It will be appreciated that elements or components shown with any embodiment herein are merely exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for treating snoring or sleep apnea of a patient, comprising:
   providing a filament implanted into a tongue of the patient adjacent the frenulum such that a proximal end of the filament exits the tongue adjacent the frenulum;
   providing a retainer including an arcuate shaped body including first and second ends and an intermediate region, the body including a connection port on the intermediate region;
   placing the body of the retainer over a plurality of lower teeth of the patient such that the connection port is located adjacent to the lower middle teeth; and
   coupling a connection member on the proximal end of the filament to the connection port to retain the tongue from moving in a posterior direction during sleep.

2. The method of claim 1, further comprising removing the connection member from the connection port after sleeping.

3. The method of claim 1, further comprising:
   removing the connection member from the connection port after sleeping; and
   removing the retainer from the patient's mouth.

4. The method of claim 1, wherein the body comprises a recess that extends between the first and second ends, and wherein placing the retainer comprises positioning a plurality of the patient's lower teeth within the recess.

5. The method of claim 4, wherein the recess has a size such that one or more molars of the patient are received in the body adjacent the first and second ends and front teeth are received at the intermediate region.

6. The method of claim 1, wherein the connection member comprises a generally spherical member attached to the proximal end of the filament, and wherein coupling a connection member comprises removably engaging the spherical member with the connection port.

7. The method of claim 1, wherein the connection port comprises a hook or curved shape element that removably receives the connection member.

8. A method for treating snoring or sleep apnea of a patient using a filament implanted in the patient's tongue such that a proximal end of the filament exits the tongue adjacent the frenulum, the method comprising:

provided a retainer including an arcuate shaped body including first and second ends and an intermediate region;

placing the retainer within the patient's oral cavity such that a connector port on the retainer is disposed adjacent front lower teeth of the patient; and coupling a connection member on the proximal end of the filament to the connector port.

9. The method of claim 8, wherein placing the retainer comprises placing the body of the retainer over a plurality of lower teeth of the patient.

10. The method of claim 8, wherein the body comprises a recess that extends between the first and second ends, and wherein placing the retainer comprises positioning a plurality of the patient's lower teeth within the recess.

11. The method of claim 10, wherein the recess has a size such that one or more molars of the patient are received in the body adjacent the first and second ends and front teeth are received at the intermediate region.

12. A method for treating snoring or sleep apnea of a patient, comprising:

securing a filament in the patient's tongue such that a proximal end of the filament exits the tongue adjacent the frenulum;

attaching a connection member to the proximal end of the filament shaped for coupling to a connection port located adjacent to the lower middle teeth of the patient; and providing a retainer including an arcuate shaped body including first and second ends and an intermediate region carrying the connection port, the body comprising a recess that extends between the first and second ends sized for receiving a plurality of the patient's lower teeth when the retainer is placed within the patient's oral cavity to position the connector port adjacent front lower teeth of the patient.

13. The method of claim 12, wherein providing a retainer comprises taking a mold of the patient's lower teeth to form the body for the retainer.

14. The method of claim 12, further comprising removing a portion of the proximal end of the filament after attaching the connection member.

15. The method of claim 12, wherein securing the filament comprises:

introducing a distal end of the filament into the tongue; and securing the distal end adjacent a back of the tongue.

16. The method of claim 15, wherein the distal end of the filament is positioned within the mucosa of the tongue adjacent the back of the tongue.

17. The method of claim 15, wherein the distal end of the filament is directed through the back of the tongue, and wherein an anchoring member is coupled to the distal end to prevent the distal end from being drawn back through the tongue.

18. The method of claim 12, wherein the connector port is formed from rigid wire formed into a hook or other curved shape to receive the connection member.

19. The method of claim 12, wherein the connector port is integrally molded into the body.

* * * * *